(12) United States Patent
Sattigeri et al.

(10) Patent No.: US 7,671,216 B2
(45) Date of Patent: Mar. 2, 2010

(54) PROCESS FOR PREPARATION OF (3R,5R)-7-[2-(4-FLUOROPHENYL)-5-ISOPROPYL-3-PHENYL-4-[(4-HYDROXY METHYL PHENYL AMINO) CARBONYL]-PYRROL-1-YL]-3,5-DIHYDROXY-HEPTANOIC ACID HEMI CALCIUM SALT

(75) Inventors: Jitendra Anant Sattigeri, Gurgaon (IN); Sachin Sethi, Yamuna Nagar (IN); Kaushal Kishore, Nalanda (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 12/092,813

(22) PCT Filed: Nov. 8, 2006

(86) PCT No.: PCT/IB2006/003153

§ 371 (c)(1),
(2), (4) Date: Jan. 6, 2009

(87) PCT Pub. No.: WO2007/054790

PCT Pub. Date: May 18, 2007

(65) Prior Publication Data

US 2009/0118520 A1 May 7, 2009

(30) Foreign Application Priority Data

Nov. 8, 2005 (IN) ........................ 2964/DEL/2005
Nov. 8, 2005 (IN) ........................ 2967/DEL/2005
Nov. 14, 2005 (IN) ........................ 3033/DEL/2005

(51) Int. Cl.
*C07D 207/30* (2006.01)
(52) U.S. Cl. ..................................... 548/561
(58) Field of Classification Search ................. 548/561
See application file for complete search history.

(56) References Cited

U.S. PATENT DOCUMENTS

| 3,262,977 A | 7/1966 | Harsanyi et al. |
|---|---|---|
| 3,341,584 A | 9/1967 | Larsen |
| 3,454,635 A | 7/1969 | Weber |
| 3,471,515 A | 10/1969 | Troxler |
| 3,483,221 A | 12/1969 | Wilhelm |
| 3,527,761 A | 9/1970 | Archibald |
| 3,562,257 A | 2/1971 | Kugita |
| 3,576,883 A | 4/1971 | Neuworth |
| 3,642,896 A | 2/1972 | Collin |
| 3,644,353 A | 2/1972 | Lunts et al. |
| 3,649,691 A | 3/1972 | Shavel |
| 3,655,663 A | 4/1972 | Wasson |
| 3,663,570 A | 5/1972 | Sato |
| 3,663,706 A | 5/1972 | Hess et al. |
| 3,669,968 A | 6/1972 | Hess |
| 3,674,836 A | 7/1972 | Creger |
| 3,705,233 A | 12/1972 | Lunts et al. |
| 3,716,583 A | 2/1973 | Nakamura et al. |
| 3,723,446 A | 3/1973 | Scherm et al. |
| 3,773,939 A | 11/1973 | Janssen |
| 3,781,328 A | 12/1973 | Witte |
| 3,850,941 A | 11/1974 | Irikura |
| 3,857,891 A | 12/1974 | Holmes et al. |
| 3,857,952 A | 12/1974 | Wooldridge et al. |
| 3,868,460 A | 2/1975 | Koppe et al. |
| 3,879,554 A | 4/1975 | Temperilli |
| 3,910,924 A | 10/1975 | Tamura et al. |
| 3,912,743 A | 10/1975 | Christensen et al. |
| 3,932,400 A | 1/1976 | Hibino et al. |
| 3,932,645 A | 1/1976 | Meyer et al. |
| 3,934,032 A | 1/1976 | Barrett et al. |
| 3,937,838 A | 2/1976 | Wetterlin et al. |
| 3,948,943 A | 4/1976 | Eberhardt et al. |
| 3,962,238 A | 6/1976 | Mauvernay et al. |
| 3,982,021 A | 9/1976 | Hauck et al. |
| 3,984,413 A | 10/1976 | Metz et al. |
| 3,994,974 A | 11/1976 | Murakami et al. |
| 3,997,666 A | 12/1976 | Witte et al. |
| 3,998,790 A | 12/1976 | Brandstrom et al. |
| 4,011,258 A | 3/1977 | Wetterlin et al. |
| 4,012,444 A | 3/1977 | Lunts et al. |
| 4,032,648 A | 6/1977 | Malen et al. |
| 4,034,009 A | 7/1977 | Zolss et al. |

(Continued)

FOREIGN PATENT DOCUMENTS

EP    0247633    12/1987

(Continued)

OTHER PUBLICATIONS

International Search Report prepared by the European Patent Office on Feb. 15, 2007 for PCT/IB2006/003153; Applicant, Ranbaxy Laboratories Limited.

(Continued)

*Primary Examiner*—Kamal A Saeed
*Assistant Examiner*—Samantha L Shterengarts
(74) *Attorney, Agent, or Firm*—Sheridan Ross P.C.

(57) ABSTRACT

The present invention relates to processes for the preparation of (3R, 5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt.

8 Claims, No Drawings

U.S. PATENT DOCUMENTS

| | | |
|---|---|---|
| 4,051,143 A | 9/1977 | Scherm et al. |
| 4,056,626 A | 11/1977 | Ito et al. |
| 4,058,552 A | 11/1977 | Mieville |
| 4,062,950 A | 12/1977 | Frommer et al. |
| 4,105,776 A | 8/1978 | Ondetti et al. |
| 4,129,565 A | 12/1978 | Fukushima et al. |
| 4,154,839 A | 5/1979 | Wehinger et al. |
| 4,182,767 A | 1/1980 | Murai et al. |
| 4,188,390 A | 2/1980 | Campbell |
| 4,217,305 A | 8/1980 | Imai et al. |
| 4,248,883 A | 2/1981 | Sawayama et al. |
| 4,252,721 A | 2/1981 | Silvestrini et al. |
| 4,252,825 A | 2/1981 | Demarne |
| 4,252,984 A | 2/1981 | Manoury et al. |
| 4,258,062 A | 3/1981 | Jonas et al. |
| 4,260,622 A | 4/1981 | Junge et al. |
| 4,264,611 A | 4/1981 | Berntsson et al. |
| 4,310,549 A | 1/1982 | Hajos et al. |
| 4,314,081 A | 2/1982 | Molloy et al. |
| 4,337,201 A | 6/1982 | Petrillo, Jr. |
| 4,344,949 A | 8/1982 | Hoefle et al. |
| 4,410,520 A | 10/1983 | Watthey |
| 4,425,355 A | 1/1984 | Hoefle et al. |
| 4,434,176 A | 2/1984 | Troxler et al. |
| 4,444,779 A | 4/1984 | Kawamatsu et al. |
| 4,448,964 A | 5/1984 | Muto et al. |
| 4,466,972 A | 8/1984 | Neumann |
| 4,470,972 A | 9/1984 | Gold et al. |
| 4,472,380 A | 9/1984 | Harris et al. |
| 4,503,067 A | 3/1985 | Wiedemann et al. |
| 4,508,729 A | 4/1985 | Vincent et al. |
| 4,522,828 A | 6/1985 | Jeffery et al. |
| 4,572,909 A | 2/1986 | Campbell et al. |
| 4,587,258 A | 5/1986 | Gold et al. |
| 4,598,089 A | 7/1986 | Hadvary et al. |
| 4,663,325 A | 5/1987 | Ohtaka et al. |
| 4,672,068 A | 6/1987 | Kutsuma et al. |
| 4,681,893 A | 7/1987 | Roth |
| 4,687,777 A | 8/1987 | Meguro et al. |
| 4,699,905 A | 10/1987 | Yanagisawa et al. |
| 4,701,559 A | 10/1987 | Horii et al. |
| 4,705,797 A | 11/1987 | Nardi et al. |
| 4,731,478 A | 3/1988 | Niigata et al. |
| 4,734,280 A | 3/1988 | Braquet |
| 4,801,599 A | 1/1989 | Semeraro et al. |
| 4,822,818 A | 4/1989 | Oka et al. |
| 4,873,259 A | 10/1989 | Summers, Jr. et al. |
| 4,879,303 A | 11/1989 | Davison et al. |
| 4,994,461 A | 2/1991 | Ulrich |
| 5,002,953 A | 3/1991 | Hindley |
| 5,049,559 A | 9/1991 | Braquet et al. |
| 5,128,355 A | 7/1992 | Carini et al. |
| 5,155,103 A | 10/1992 | Weber et al. |
| 5,155,120 A | 10/1992 | Lazar et al. |
| 5,185,351 A | 2/1993 | Finkelstein et al. |
| 5,273,995 A | 12/1993 | Roth |
| 5,274,094 A | 12/1993 | Whittaker et al. |
| 5,344,914 A | 9/1994 | Gibson et al. |
| 5,349,056 A | 9/1994 | Panayotatos |
| 5,356,896 A | 10/1994 | Kabadi et al. |
| 5,385,929 A | 1/1995 | Bjorge et al. |
| 5,399,578 A | 3/1995 | Buhlmayer et al. |
| 5,422,351 A | 6/1995 | Piwinski et al. |
| 5,424,286 A | 6/1995 | Eng |
| 5,466,823 A | 11/1995 | Talley et al. |
| 5,474,995 A | 12/1995 | Ducharme et al. |
| 5,491,172 A | 2/1996 | Lee et al. |
| 5,492,906 A | 2/1996 | Braquet et al. |
| 5,510,332 A | 4/1996 | Kogan et al. |
| 5,541,183 A | 7/1996 | Park et al. |
| 5,552,438 A | 9/1996 | Christensen, IV |
| 5,559,233 A | 9/1996 | Bernhart et al. |
| 5,624,941 A | 4/1997 | Barth et al. |
| 5,633,272 A | 5/1997 | Talley et al. |
| 5,693,675 A | 12/1997 | Mandeville, III et al. |
| 5,712,298 A | 1/1998 | Amschler |
| 5,733,931 A | 3/1998 | Yamada et al. |
| 5,744,501 A | 4/1998 | Norden |
| 5,753,653 A | 5/1998 | Bender et al. |
| 5,767,115 A | 6/1998 | Rosenblum et al. |
| 5,932,598 A | 8/1999 | Talley et al. |
| 5,968,982 A | 10/1999 | Voss et al. |
| 5,985,322 A | 11/1999 | Anderson et al. |
| 5,990,173 A | 11/1999 | Patoiseau et al. |
| 5,994,510 A | 11/1999 | Adair et al. |
| 6,015,557 A | 1/2000 | Tobinick et al. |
| 6,147,090 A | 11/2000 | DeNinno et al. |
| 6,197,786 B1 | 3/2001 | DeNinno et al. |
| 6,268,392 B1 | 7/2001 | Keller et al. |
| 6,329,336 B1 | 12/2001 | Bridon et al. |
| 6,329,344 B1 | 12/2001 | Arora et al. |
| 6,395,751 B1 | 5/2002 | DeNinno et al. |
| 6,420,417 B1 | 7/2002 | Keller et al. |
| 6,426,365 B1 | 7/2002 | Shinkai et al. |
| 6,489,478 B1 | 12/2002 | DeNinno et al. |
| 6,511,985 B1 | 1/2003 | Ippen et al. |
| 6,534,088 B2 | 3/2003 | Guivarc'h et al. |
| 6,569,461 B1 | 5/2003 | Tilyer et al. |
| 6,586,448 B1 | 7/2003 | DeNinno et al. |
| 6,590,085 B1 | 7/2003 | Arora et al. |
| 6,642,268 B2 | 11/2003 | Keller et al. |
| 6,753,346 B2 | 6/2004 | Shinkai et al. |
| 6,787,570 B2 | 9/2004 | Sikorski et al. |
| 6,794,396 B2 | 9/2004 | Lee et al. |
| 6,803,388 B2 | 10/2004 | Sikorski et al. |
| 6,884,226 B2 | 4/2005 | Pereira |
| 7,056,936 B2 | 6/2006 | Kilian et al. |
| 7,361,772 B2 | 4/2008 | Mathew et al. |
| 2002/0052312 A1 | 5/2002 | Reiss et al. |
| 2003/0153617 A1 | 8/2003 | Dalen et al. |
| 2004/0029962 A1 | 2/2004 | Chen et al. |
| 2004/0053842 A1 | 3/2004 | Nguyen et al. |
| 2004/0097555 A1 | 5/2004 | Ohkawa et al. |
| 2004/0132771 A1 | 7/2004 | Babcock et al. |
| 2005/0032878 A1 | 2/2005 | Deboeck et al. |
| 2005/0063911 A1 | 3/2005 | Nilsson et al. |
| 2005/0187204 A1 | 8/2005 | Kondo et al. |
| 2007/0238716 A1 | 10/2007 | Murthy et al. |
| 2007/0259874 A1 | 11/2007 | Palle et al. |
| 2008/0153896 A1 | 6/2008 | Yadav et al. |
| 2008/0248035 A1 | 10/2008 | Sattigeri et al. |
| 2008/0287690 A1 | 11/2008 | Kaul et al. |

FOREIGN PATENT DOCUMENTS

| | | |
|---|---|---|
| EP | 0409281 | 1/1991 |
| EP | 0419049 | 3/1991 |
| EP | 0542355 | 5/1993 |
| EP | 0542356 | 5/1993 |
| EP | 0606646 | 7/1994 |
| EP | 0651739 | 5/1995 |
| EP | 0680963 | 11/1995 |
| EP | 0753298 | 1/1997 |
| EP | 0818197 | 1/1998 |
| EP | 0818448 | 1/1998 |
| EP | 0842943 | 5/1998 |
| EP | 0903353 | 3/1999 |
| EP | 0905139 | 3/1999 |
| EP | 0918059 | 5/1999 |
| EP | 1488808 | 12/2004 |
| EP | 1510208 | 3/2005 |
| EP | 1523316 | 4/2005 |
| RU | 2279430 | 7/2006 |
| UA | 72290 | 9/2002 |

| | | |
|---|---|---|
| WO | WO 95/15973 | 6/1995 |
| WO | WO 95/28926 | 11/1995 |
| WO | WO 96/01644 | 1/1996 |
| WO | WO 96/06108 | 2/1996 |
| WO | WO 96/20216 | 7/1996 |
| WO | WO 96/22966 | 8/1996 |
| WO | WO 96/31206 | 10/1996 |
| WO | WO 96/40641 | 12/1996 |
| WO | WO 96/40781 | 12/1996 |
| WO | WO 97/02289 | 1/1997 |
| WO | WO 97/03094 | 1/1997 |
| WO | WO 97/16184 | 5/1997 |
| WO | WO 97/22619 | 6/1997 |
| WO | WO 98/19998 | 5/1998 |
| WO | WO 98/27098 | 6/1998 |
| WO | WO 98/47892 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 99/20110 | 4/1999 |
| WO | WO 99/23063 | 5/1999 |
| WO | WO 99/24398 | 5/1999 |
| WO | WO 99/35163 | 7/1999 |
| WO | WO 99/36393 | 7/1999 |
| WO | WO 99/37605 | 7/1999 |
| WO | WO 99/37618 | 7/1999 |
| WO | WO 99/43642 | 9/1999 |
| WO | WO 99/47138 | 9/1999 |
| WO | WO 99/47547 | 9/1999 |
| WO | WO 99/54321 | 10/1999 |
| WO | WO 99/58505 | 11/1999 |
| WO | WO 99/58902 | 11/1999 |
| WO | WO 99/61465 | 12/1999 |
| WO | WO 99/67230 | 12/1999 |
| WO | WO 00/00477 | 1/2000 |
| WO | WO 00/01690 | 1/2000 |
| WO | WO 00/05223 | 2/2000 |
| WO | WO 00/05224 | 2/2000 |
| WO | WO 00/15612 | 3/2000 |
| WO | WO 00/18759 | 4/2000 |
| WO | WO 00/18760 | 4/2000 |
| WO | WO 00/35425 | 6/2000 |
| WO | WO 00/43384 | 7/2000 |
| WO | WO 01/13953 | 3/2001 |
| WO | WO 01/32127 | 5/2001 |
| WO | WO 01/37831 | 5/2001 |
| WO | WO 01/42246 | 6/2001 |
| WO | WO 01/93860 | 12/2001 |
| WO | WO 02/096422 | 12/2002 |
| WO | WO 03/007993 | 1/2003 |
| WO | WO 03/013607 | 2/2003 |
| WO | WO 03/013608 | 2/2003 |
| WO | WO 03/066063 | 8/2003 |
| WO | WO 03/077896 | 9/2003 |
| WO | WO 03/080070 | 10/2003 |
| WO | WO 03/088962 | 10/2003 |
| WO | WO 03/094923 | 11/2003 |
| WO | WO 2004/004777 | 1/2004 |
| WO | WO 2004/004778 | 1/2004 |
| WO | WO 2004/014896 | 2/2004 |
| WO | WO 2004/019985 | 3/2004 |
| WO | WO 2004/028456 | 4/2004 |
| WO | WO 2004/039373 | 5/2004 |
| WO | WO 2004/056359 | 7/2004 |
| WO | WO 2004/056395 | 7/2004 |
| WO | WO 2004/062557 | 7/2004 |
| WO | WO 2004/067006 | 8/2004 |
| WO | WO 2004/098583 | 11/2004 |
| WO | WO 2004/106299 | 12/2004 |
| WO | WO 2005/009340 | 2/2005 |
| WO | WO 2005/014539 | 2/2005 |
| WO | WO 2005/018626 | 3/2005 |
| WO | WO 2005/021515 | 3/2005 |
| WO | WO 2005/026163 | 3/2005 |
| WO | WO 2005/034908 | 4/2005 |
| WO | WO 2005/041864 | 5/2005 |
| WO | WO 2005/051931 | 6/2005 |
| WO | WO 2005/056536 | 6/2005 |
| WO | WO 2005/058813 | 6/2005 |
| WO | WO 2005/058898 | 6/2005 |
| WO | WO 2005/100318 | 10/2005 |
| WO | WO 2005/100331 | 10/2005 |
| WO | WO 2006/085212 | 8/2006 |
| WO | WO 2006/117743 | 11/2006 |
| WO | WO 2007/054789 | 5/2007 |
| WO | WO 2007/054790 | 5/2007 |
| WO | WO 2007/054896 | 5/2007 |

OTHER PUBLICATIONS

"Prevent" definition from dictionary.com, accessed Nov. 28, 2007.
Bedford et al., "Nonquaternary Cholinesterase Reactivators. 3. 3(5)-Substituted 1,2,4-Oxadiazol-5(3)-aldoximes and 1,2,4-Oxidiazole-5(3)-thiocarbohydroximates as Reactivators of Organophosphonate-Inhibited Eel and Human Acetylcholinesterase in Vitro", Journal of Medicinal Chemistry, 29(11):2174-2183 (1986).
Carr et al., "Enzymatic Determination of Triglyceride, Free Cholesterol, and Total Cholesterol in Tissue Lipid Extracts", Clin. Biochem., 26:39-42 (1993).
Ruys et al., "The Estimation of Serum Triglycerides by Nephelometry: A Simple Method for the Estimation of Serum Triglycerides Suitabe for the Small Laboratory", Med. J. Aust., 22(1):385-387 (1975).
Niculescu-Duvaz D et al., "Self-Immolative Nitrogen Mustard Profdrugs for Suicide Gene Therapy", J. Med. Chem. 41(26):5297-5309 (1998).
Nakanishi, K., "Terpene trilactones from Gingko bioloba: From ancient times to the 21st century", Bioorg. Med. Chem., 13:4987-5000 (2005).
Rinaldi-Carmona et al., "Biochemical and Pharmacological Characterisation of SR141716A, the first potent and selective brain cannabinoid receptor antagonist", Life Sci., 56:1941-1947 (1995).
Rodriguez-Sureda et al., "A Procedure for measuring triacylglyceride and cholesterol content using a small amount of tissue", Anal. Biochem., 343:277-282 (2005).
Karimi et al., "*Lithium triflate* (LiOTf) catalyzed efficient and chemoselective tetrahydropyranylation of alcohols and phenols under mild and neutral reaction conditions", Tetrahedron Lett., 43(30):5353 (2002).
Wilson et al., "Estimation of VLDL cholesterol in hyperlipidemia", Clin. Chim. Acta., Oct. 15; 1513:285-291 (1985).
Zhang et al., "Niacin mediates lipolysis in adipose tissue through its G-protein coupled receptor HM74A", Biochem and Biophys. Res. Commun., 334:729-732 (2005).
Examination Report for European Patent Application No. 06820873.5, dated Mar. 25, 2009.
International Preliminary Report on Patentability for International (PCT) Patent Application No. PCT/IB2006/003153, mailed May 22, 2008.
U.S. Appl. No. 10/558,859, filed Nov. 30, 2005, Salman et al.
Allain et al., Clin. Chem., 20:470 (1974).
Antibacterial & Antifungal Drug Discovery & Development Summit, Strategic Research Institute, Jun. 28-29, 2001, Amsterdam, The Netherlands.
Baumann et al., "The Convergent Synthesis of CI-981, an Optically Active, Highly Potent, Tissue Selective Inhibitor of HMG-COA Reductase", Tetrahedron Letters, Elsevier, vol. 33, No. 17, Apr. 21, 1992, pp. 2283-2284.
Bedford et al., "Nonquaternary Cholinesterase Reactivators. 3. 3(5)-Substituted 1,2,4-Oxadiazol-5(3)-aldoximes and 1,2,4-Oxidiazole-5(3)-thiocarbohydroximates as Reactivators of Organophosphonate-Inhibited Eel and Human Acetylcholinesterase in Vitro", Journal of Medicinal Chemistry, 29(11):2174-2183 (1986).
Cui et al., J. Biol. Chem., 278:10214-10220 (2003).
Dolinsky et al., Biochem. J., 378:967-974 (2004).

Frederikson et al., J. Lipid Res., 45:592-601 (2004).

Friedewald et al., Clin. Chem., 18:6, pp. 499-502 (1972).

Frings et al., Clin. Chem., 18(7), pp. 673-674 (1972).

Fujino et al., "Metabolic properties of the acid and lactone froms of HMG-CoA reductasse inhibitors", Xenobiotica, Nov./Dec. 2004, vol. 34, No. 11/12, pp. 961-971.

Harwood et al., J. Lipid Res., 34:377-395 (1993).

Heller et al., "Solubilization and Partial Purification of Hepatic 3-Hydroxy-3Methylglutaryl Coenzyme a Reductase," Biochemical and Biophysical Research Communications, 50(3): 859-865 (1973).

Kubo and Strott, "Differential Activity of 3-Hydroxy-3-Methylglutaryl Coenzyme a Reductase in Zones of the Adrenal Cortex," Endocrinology, 120(1):214-221 (1987).

Lorenzen et al., Mol. Pharmacol., 59:349-357 (2001).

Meyer et al., "Annulation of a,b-Unsaturated Ketones by a Micael Addition-Cyclization Sequence. A Versatile Syntesis of Alicyclic Six-Membered Rings", Journal of Organice Chemistry, 50(4):438-447 (1985).

Renodon-Corniere et al., "N-Aryl N'Hydroxyguanidines, A New Class of NO-Donors after Selective Oxidation by Nitric Oxide Synthases: Structure-Activity Relationship," Journal of Medicinal Chemistry, 45(4):944-954 (2002).

Rifai et al., Clin. Chem., 32(6):957-961 (1986).

Sampson et al., Clin. Chem., 47(3):532-539 (2001).

Shefer et al., J. Lipid Res., 22:532-536 (1981).

Sun et al., "A general Sythesis of dioxolenone prodrug moieties", Tetrahedron Letters, 43:1161-1164 (2002).

U.S. Appl. No. 60/498,947, filed Aug. 29, 2003, entitled "Isoxazoline derivatives as inhibitors or phophodiesterase type-IV".

Written Opinion for International (PCT) Patent Application No. PCT/IB2006/003153, mailed Feb. 27, 2007.

International Preiliminary Report on Patentability for International (PCT) Patent Application No. PCT/IB2006/003153, mailed May 22, 2008.

PROCESS FOR PREPARATION OF (3R,5R)-7-[2-(4-FLUOROPHENYL)-5-ISOPROPYL-3-PHENYL-4-[(4-HYDROXY METHYL PHENYL AMINO) CARBONYL]-PYRROL-1-YL]-3,5-DIHYDROXY-HEPTANOIC ACID HEMI CALCIUM SALT

CROSS REFERENCE TO RELATED APPLICATIONS

This application is a national stage application under 35 U.S.C. §371 of PCT Application No. PCT/IB2006/003153 having an international filing date of Nov. 8, 2006, which designated the United States, which claims the benefit of priority to Indian Patent Application No. 2964/DEL/2005, filed Nov. 8, 2005; Indian Patent Application No. 2967/DEL/2005, filed Nov. 8, 2005, and Indian Patent Application No. 3033/DEL/2005, filed Nov. 14, 2005. The entire disclosure of these patent documents is hereby by reference.

FIELD OF THE INVENTION

The present invention relates to processes for the preparation of (3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt.

BACKGROUND OF THE INVENTION (3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt acts an inhibitor of 3-hydroxy-3-methylglutaryl-coenzyme A (HMG-CoA) reductase, a coenzyme catalyzing the intracellular synthesis of cholesterol, and thus is useful as hypolipidemic and hypocholesterolemic agent, as discussed in PCT Publication No. 04/106299.

Cardiovascular disease and its associated maladies, dysfunctions and complications are a principal cause of disability and the chief cause of death. One specific factor significantly contributing to this pathophysiologic process is atherosclerosis, which has been generally recognized as the leading health care problem both with respect to mortality and health care costs.

Atherosclerosis is characterized by the deposition of fatty substances, primarily cholesterol, resulting in plaque formation on the inner surface of the arterial wall and degenerative change to the arteries. It is now well established that cardiovascular disorders including myocardial infarction, coronary heart disease, hypertension and hypotension, cerebrovascular disorders including stroke, cerebral thrombosis and memory loss due to stroke; peripheral vascular disease and intestinal infarction are caused by blockage of arteries and arterioles by atherosclerotic plaque. Atherosclerotic plaque formation is multi-factorial in its production. Hypercholesterolemia, especially elevated levels of low-density lipoprotein cholesterol (LDL), is an important risk factor for atherosclerosis and arteriosclerosis and associated diseases.

The HMG-CoA reductase inhibitors (statins) have been used in reducing blood levels of LDL cholesterol. Cholesterol is produced via the mevalonic acid pathway. Reducing the formation of mevalonic acid, a precursor to cholesterol, leads to a corresponding decrease in hepatic cholesterol biosynthesis with a reduction in the cellular pool of cholesterol.

A synthetic procedure for preparing (3R,5R)-7-[2-(4-fluorophenyl)-5-isopropyl-3-phenyl-4-[(4-hydroxy methyl phenyl amino) carbonyl]-pyrrol-1-yl]-3,5-dihydroxy-heptanoic acid hemi calcium salt has been disclosed in PCT Publication No. WO 04/106299. The aforementioned procedure involves multiple steps involving selective hydrolysis of two chemically similar functionalities e.g. hydrolysis of methyl ester in the presence of tert.-butyl ester, and reduction with sodium borohydride in the presence of iodine or with borane dimethyl sulphide which are expensive reagents and are air- and moisture-sensitive, hence difficult to handle.

SUMMARY OF THE INVENTION

Accordingly, herein are provided processes for preparing (3R,5R)-7-[2-(4-fluorophenyl)-5-isopropyl-3-phenyl-4-[(4-hydroxy methyl phenyl amino) carbonyl]-pyrrol-1-yl]-3,5-dihydroxy-heptanoic acid hemi calcium salt by using synthetic procedure incorporating particular intermediates.

Further, herein are provided processes which are simple and economical, avoid the use of expensive and air- and moisture-sensitive reagents, and avoid selective hydrolysis of methyl ester in the presence of tert-butyl ester.

Further, herein are provided processes for the preparation of a compound of Formula I

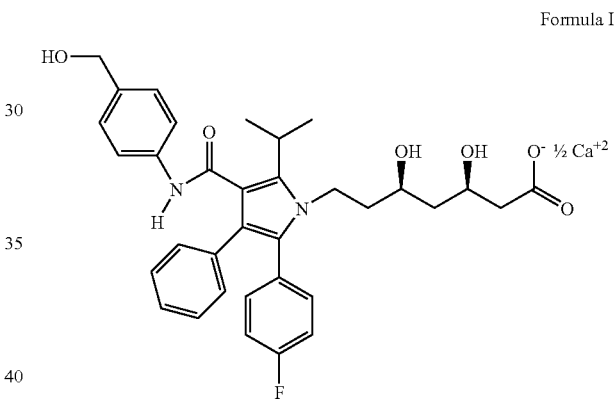

Formula I which processes comprise:

(a) reacting an amine of Formula II with methyl isobutyryl acetate of Formula III Formula II Formula III to form a compound of Formula of IV (wherein R is a hydroxy protecting group, for example, acetyl, benzoyl, tetrahydropyranyl, methoxy methyl, methoxy ethoxymethyl, benzyl);

Formula IV

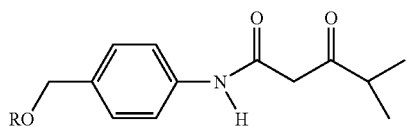

b) reacting the compound of Formula IV with benzaldehyde to form a compound of Formula V;

Formula V

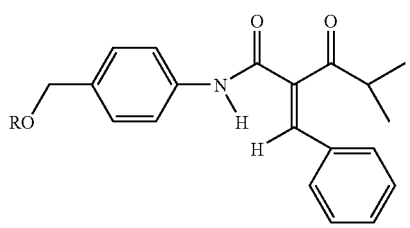

c) reacting the compound of Formula V with 4-fluorobenzaldehyde to form a compound of Formula VI;

Formula VI

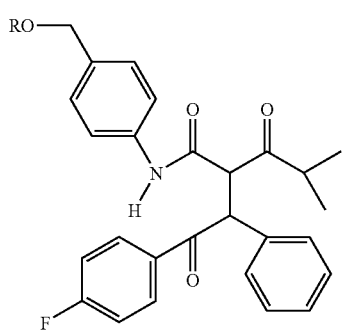

d) reacting the compound of Formula VI with a compound of Formula VII

Formula VII

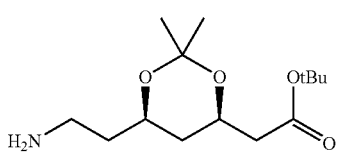

to form a compound of Formula VIII;

Formula VIII

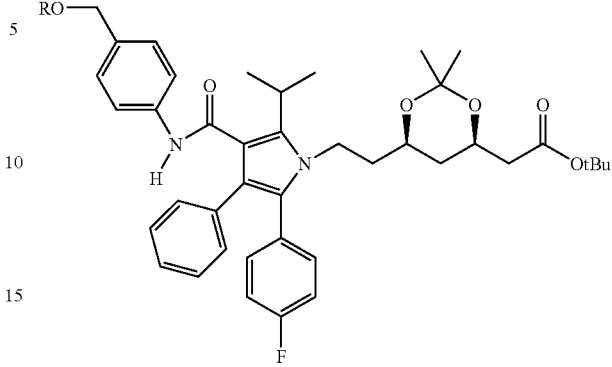

e) subjecting the compound of Formula VIII simultaneously to acid-catalyzed cleavage of ketal and hydroxy protecting group (when R is tetrahydropyranyl) to form a compound of Formula IX;

Formula IX

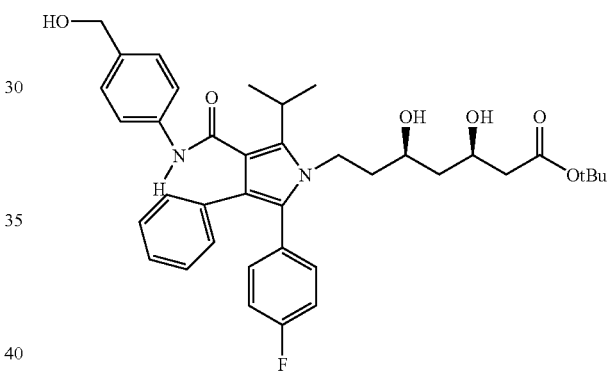

f) subjecting the compound of Formula IX to base-catalyzed hydrolysis to form a compound of Formula X; and Formula X

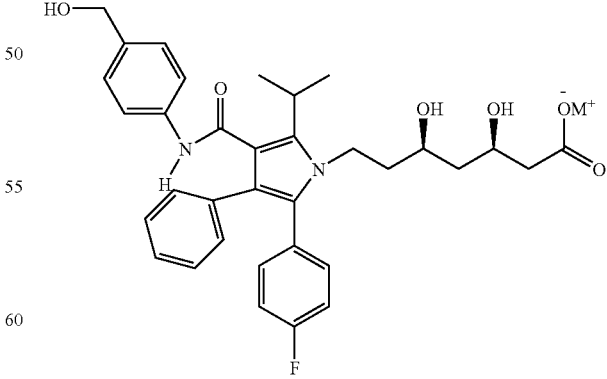

(wherein, M = Li, Na or K)

g) reacting the compound of Formula X with an aqueous solution of calcium acetate to form a compound of Formula I.

This process may involve one or more of the following features. For example, reaction of an amine of Formula II can be carried out in the presence of one or more organic bases such as, for example, triethylamine, pyridine, 1,2-ethylenediamine or mixtures thereof, in one or more aromatic solvents, for example, xylene, toluene or mixtures thereof. In another feature, the reaction of a compound of Formula IV can be carried out in the presence of one or more organic bases such as, for example, piperidine, pyridine, β-alanine or mixtures thereof, one or more organic acids such as, for example, glacial acetic acid or benzoic acid or mixture of organic bases and organic acids, in one or more solvents such as, for example, hydrocarbon solvents (e.g., hexane or heptane), halogenated solvents (e.g., dichloromethane, dichloroethane or chloroform), aromatic solvents (e.g., toluene or xylene) or mixtures thereof. In another feature, the reaction of a compound of Formula V can be carried out in the presence of one or more catalysts such as, for example, sodium cyanide, 3-ethyl-5-(2-hydroxyethyl)-4-methyl thiazolium bromide, 3-benzyl-5-(2-hydroxyethyl)-4-methyl thiazolium chloride or mixtures thereof, one or more organic bases such as, for example, triethylamine, pyridine or mixtures thereof, in a solvent-free condition or in one or more solvents such as, for example, protic polar solvents (e.g., methanol, ethanol, propanol, isopropanol or water), ethers (e.g., dioxan or tetrahydrofuran) or mixtures thereof. In another feature, the reaction of a compound of Formula VI can be carried out in the presence of one or more organic acids such as, for example, pivalic acid, p-toluene sulfonic acid or mixtures thereof, in one or more solvents such as, for example, aromatic solvents (e.g., xylene or toluene), hydrocarbon solvents (e.g., hexane or heptane), ethers (e.g., tetrahydrofuran, dioxane or diethyl ether) or mixtures thereof. In another feature, the cleavage of ketal and hydroxy protecting group of a compound of Formula VIII can be carried out in the presence of one or more mineral acids such as, for example, hydrochloric acid, hydrobromic acid, hydroiodic acid or mixtures thereof, in one or more solvents such as, for example, protic polar solvents (e.g., methanol, ethanol, propanol or water), ethers (e.g., tetrahydrofuran or diethyl ether) or mixtures thereof. In yet another feature, the hydrolysis of a compound of Formula IX can be carried out in the presence of one or more bases such as, for example, lithium hydroxide, sodium hydroxide, potassium hydroxide or mixtures thereof, in one or more solvents such as, for example, protic polar solvents (e.g., methanol, ethanol, propanol, isopropanol or water), ethers (e.g., tetrahydrofuran or diethyl ether) or mixtures thereof.

DETAILED DESCRIPTION OF THE INVENTION (3R,5R)-7-[2-(4-fluorophenyl)-5-isopropyl-3-phenyl-4-[(4-hydroxy methyl phenyl amino) carbonyl]-pyrrol-1-yl]-3,5-dihydroxy-heptanoic acid hemi calcium salt described herein may be prepared by following, for example, reaction sequences as depicted in Scheme I.

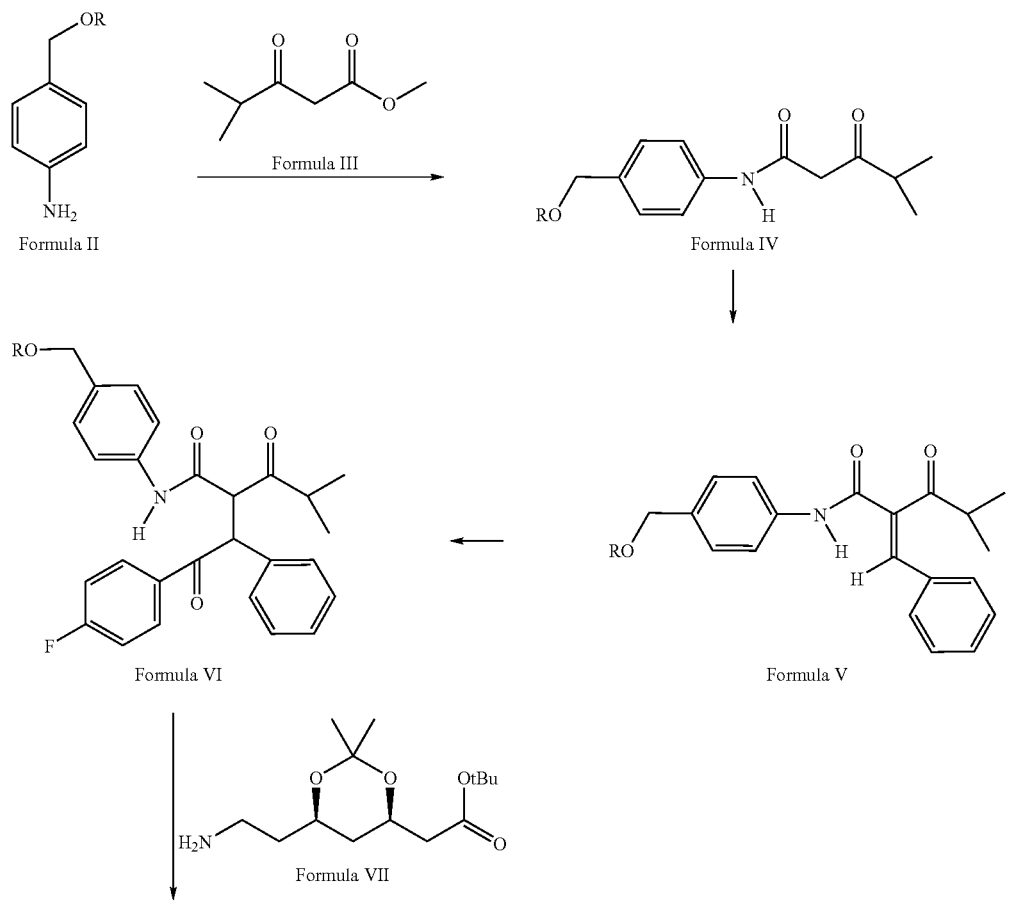

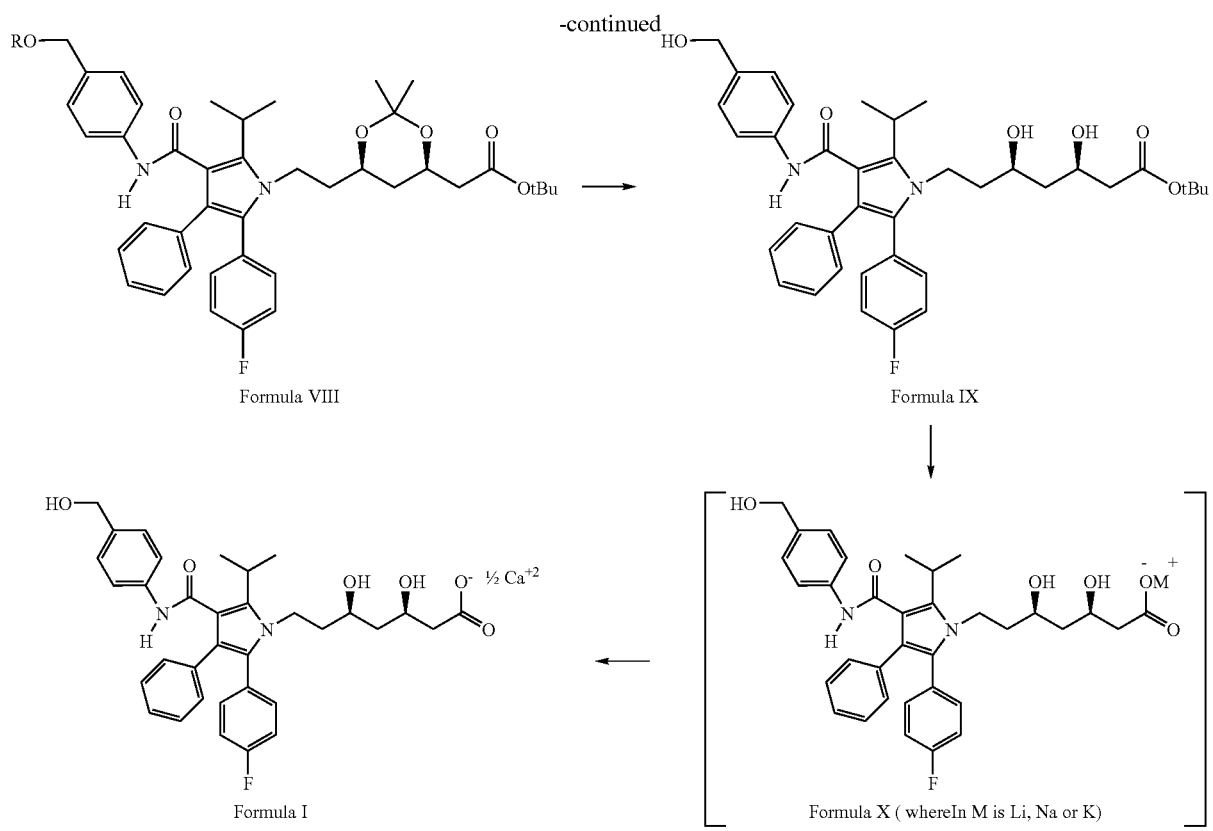

Formula VIII

Formula IX

Formula I

Formula X (wherein M is Li, Na or K)

(3R,5R)-7-[2-(4-fluorophenyl)-5-isopropyl-3-phenyl-4-[(4-hydroxy methyl phenyl amino) carbonyl]-pyrrol-1-yl]-3,5-dihydroxy-heptanoic acid hemi calcium salt of Formula I can be prepared, for example, according to Scheme I. Thus, an amine of Formula I can be reacted with methyl isobutyryl acetate of Formula III to form a compound of Formula of IV (wherein R is the same as defined earlier). The compound of Formula IV can be reacted with benzaldehyde to form a compound of Formula V. The compound of Formula V can be reacted with 4-fluorobenzaldehyde to form a compound of Formula VI. The compound of Formula VI can be reacted with a compound of Formula VII to form a compound of Formula VIII. The compound of Formula VIII can be simultaneously subject to acid catalyzed cleavage of ketal and hydroxy protecting group (when R is tetrahydropyranyl) to form a compound of Formula IX. The compound of Formula IX can be subject to alkali base catalyzed hydrolysis to form a compound of Formula X. The compound of Formula X can be further converted to hemi calcium salt of Formula I by following procedures known to those of skill in the art.

The reaction of an amine of Formula II can be carried out in one or more aromatic solvents, for example, xylene, toluene or mixtures thereof. The reaction can also be carried out in the presence of one or more organic bases, for example, triethylamine, pyridine, 1,2-ethylenediamine or mixtures thereof.

The reaction of a compound of Formula IV can be carried out in one or more solvents, for example, hydrocarbon solvents (e.g., hexane or heptane), or halogenated solvents (e.g., dichloromethane, dichloroethane or chloroform), aromatic solvents (e.g., toluene or xylene) or mixtures thereof. The reaction can also be carried out in the presence of one or more organic bases, for example, piperidine, pyridine or β-alanine, one or more organic acids, for example, glacial acetic acid or benzoic acid or mixtures of organic bases and organic acids.

The reaction of a compound of Formula V can be carried out in the presence of one or more catalysts, for example, sodium cyanide, 3-ethyl-5-(2-hydroxyethyl)-4-methyl thiazolium bromide, 3-benzyl-5-(2-hydroxyethyl)-4-methyl thiazolium chloride or mixtures thereof. The reaction can also be carried out in the presence of one or more organic bases, for example, triethylamine, pyridine or mixture thereof, in a solvent-free condition or in one or more solvents, for example, protic polar solvents (e.g., methanol, ethanol, propanol, isopropanol or water), ethers (e.g., dioxan or tetrahydrofuran) or mixtures thereof.

The reaction of a compound of Formula VI can be carried out in one or more solvents, for example, aromatic solvents (e.g., xylene or toluene), hydrocarbon solvents (e.g., hexane or heptane), ethers (e.g., tetrahydrofuran, dioxane or diethyl ether) or mixtures thereof. The reaction can also be carried out in the presence of one or more organic acids, for example, pivalic acid, p-toluene sulfonic acid or mixtures thereof.

The cleavage of ketal and hydroxy protecting group of a compound of Formula VIII can be carried out in the presence of one or more mineral acids, for example, hydrochloric acid, hydrobromic acid, hydroiodic acid or mixtures thereof. The reaction can also be carried out in one or more solvents, for example, protic polar solvents (e.g., methanol, ethanol, propanol or water), ethers (e.g., tetrahydrofuran or diethyl ether) or mixtures thereof. The cleavage of ketal and hydroxy protecting group can also be carried out by any other cleavage method known to those of skill in the art.

The hydrolysis of a compound of Formula IX can be carried out in the presence of one or more bases, for example, lithium hydroxide, sodium hydroxide, potassium hydroxide or mixtures thereof. The reaction can also be carried out in one or more solvents, for example, protic polar solvents (e.g., methanol, ethanol, propanol, isopropanol or water), ethers (e.g., tetrahydrofuran or diethyl ether) or mixtures thereof.

The compound of Formula X can be converted into its corresponding hemi calcium salt of Formula I by following procedure known to those of skill in the art.

In the above schemes, where specific reducing agents, solvents, bases, catalysts, acids etc., are mentioned, it is to be understood that other reducing agents, solvents, bases, catalysts, acids etc., known to those skilled in the art may be used. Similarly, the reaction temperature and duration may be adjusted.

While the present invention has been described in terms of its specific embodiments, certain modifications and equivalents will be apparent to those skilled in the art and are within the scope of the present invention.

EXAMPLES

Example 1

Preparation of 4-methyl-3-oxo-pentanoic acid [4-(tetrahydropyran-2-yloxymethyl)phenyl]amide A mixture of 4-(tetrahydropyran-2-yloxymethyl)phenyl amine (70 g, 0.34 mol, 1 equiv.) (prepared following the procedure mentioned in *J. Med. Chem.*, 41, 26, (1998), 5297-5309; and *Tetrahedron Lett.*, 43, 30, (2002), 5353), methyl isobutyryl acetate (49 g, 0.34 mol, 1 equiv.), toluene (600 mL) and 1,2-ethylenediamine (2.0 g, 0.034 mol, 0.1 equiv.) was placed in a 2-necked round bottom flask and the reaction mixture was refluxed under a Dean-Stark set up. After completion of the reaction, the solvent was removed under vacuum. The crude product was taken as such for next step. Yield: 116 g (crude)

MS (+ion mode): m/z 320.16 (M+1); $^1$H NMR (CDCl$_3$, 300 Hz): δ 1.27 (d, J=6 Hz, 6H); 1.33 (s, 2H); 1.54-1.72 (m, 7H); 2.74 (sep, J=6 Hz, 1H); 3.52-3.56 (m, 1H); 3.61 (s, 2H); 3.87-3.95 (m, 1H); 4.47 (d, J=12 Hz, 1H); 4.68 (m, 1H); 4.74 (d, J=12 Hz, 1H); 7.32 (d, J=9 Hz, 2H); 7.53 (d, J=6 Hz, 2H); 9.22 (brs, 1H).

Example 2

Preparation of 2-benzylidine-4-methyl-3-oxo-pentanoic acid [4-(tetrahydro-pyran-2-yloxy methyl)phenyl]amide A mixture of crude 4-methyl-3-oxo-pentanoic acid [4-(tetrahydropyran-2-yloxy methyl)phenyl]amide (100 g, 0.31 mol, 1 equiv.), β-alanine (5.6 g, 0.063 mol, 0.2 equiv.), benzaldehyde (30.5 mL, 0.31 mol, 1 equiv.), glacial acetic acid (10.6 mL, 0.19 mol, 0.6 equiv.) and hexane (500 mL) was placed in a 2 necked-flask equipped with a Dean-Stark setup. The reaction mixture was refluxed with azeotropic removal of water. At the end of the reaction (TLC monitoring) the solvent was evaporated under reduced pressure to give solid, which was washed with hot hexane, and the solid was collected on a Buchner funnel. The crude compound was purified on column (silica gel, 100-200 mesh, 15% ethyl acetate/hexane) to afford the pure product. Yield: 66.81 g (52.36%).

MS (+ion mode): m/z 408.12 (M+1); $^1$H NMR (CDCl$_3$, 300 Hz): δ 1.22 (d, J=6.0 Hz, 6H); 1.52-1.85 (m, 8H); 3.35 (sep, J=6 Hz, 1H); 3.52-3.56 (m, 1H); 3.87-3.91 (m, 1H); 4.47 (d, J=12 Hz, 1H); 4.68-4.7 (m, 1H); 4.75 (d, J=12 Hz, 1H); 7.32-7.64 (m, 11H).

Example 3

Preparation of 2-[2-(4-fluorophenyl)-2-oxo-1-phenylethyl]-4-methyl-3-oxo-pentanoic acid [4-(tetrahydropyran-2-yloxy methyl phenyl]amide A mixture of 2-benzylidine-4-methyl-3-oxo-pentanoic acid [4-(tetrahydro-pyran-2-yloxy methyl)phenyl]amide (5.0 g, 0.012 mol, 1 equiv.), 4-fluorobenzaldehyde (1.5 mL, 0.0013 mol, 1.1 equiv.), 3-ethyl-5-(2-hydroxyethyl)-4-methyl thiazolium bromide (0.77 g, 0.0003 mol, 0.25 equiv.), triethyl amine (dry, 10 mL, 0.0072 mol, 5.8 equiv.) were placed in round bottom flask, and purged with nitrogen gas. The reaction mixture was refluxed at 90° C. for about 6 hours. After the reaction was over, the reaction mixture was extracted with ethyl acetate and washed with water, and dried over anhydrous sodium sulphate. Organic layer was concentrated and the crude mixture was purified on column (silica gel, 100-200 mesh, 17% ethyl acetate/hexane) to afford the pure product. Yield: 2.52 g (38.6%)

MS (+ion mode): m/z 532.17 (M+1); $^1$H NMR (CDCl$_3$, 300 Hz): δ 1.15 (d, J=6.0 Hz, 3H); 1.23 (d, J=6.0 Hz, 3H); 1.45-1.851 (m, 6H); 2.85-3.05 (m, 1H); 3.20-3.55 (m, 1H); 3.70-3.95 (m, 1H); 4.40-4.53 (m, 2H); 4.67-4.72 (m, 2H); 5.34 (d, J=9.0 Hz, 1H); 7.01-7.28 (m, 12H); 7.95-8.00 (m, 2H).

Example 4

Preparation of [(4R,6R)-6-(2-{2-(4-fluorophenyl)-5-isopropyl-3-phenyl-4-[4-(tetrahydropyran-2-yloxy methyl)phenyl amino)carbonyl]pyrrol-1-yl}ethyl)-2,2-dimethyl-[1,3]dioxan-4-yl]-acetic acid tert-butyl ester A mixture of 2-[2-(4-fluorophenyl)-2-oxo-1-phenylethyl]-4-methyl-3-oxo-pentanoic acid [4-(tetrahydropyran-2-yloxy methyl)phenyl]amide (2.0 g, 0.004 mol, 1 equiv.), an amine of Formula IX (1.5 g, 0.006 mol, 1.5 equiv.), pivalic acid (0.45 mL, 0.004 mol, 1.03 equiv.), and heptane:toluene:tetrahydrofuran (4:1:1, 24 ml) was placed in a round bottom flask equipped with a Dean-Stark setup. The reaction mixture was refluxed at with azeotropic removal of water. After the completion of reaction (TLC monitoring), the solvents were removed on a rotary evaporator. The residue was diluted with ethyl acetate and a saturated solution of sodium bicarbonate was added to this solution. The aqueous layer was extracted with ethyl acetate and the organic layer was washed with water, brine, dried over anhydrous sodium sulphate and concentrated. The crude mixture was purified on column (silica gel, 100-200 mesh, 15% ethyl acetate/hexane) to obtain the pure product. Yield: 1.0 g (34.6%).

MS (+ion mode): m/z 769.45 (M+1); $^1$H NMR (CDCl$_3$, 300 Hz): δ 0.9-1.1 (m, 2H); 1.30 (s, 1H), 1.36 (s, 3H); 1.43 (s, 9H); 1.50-1.77 (m, 14 6H); 2.20-2.40 (m, 2H); 3.52-3.70 (m, 3H); 3.85-3.89 (m, 2H); 4.05-4.25 (m, 2H); 4.40 (d, J=12 Hz, 1H); 4.64-4.70 (m, 2H); 6.86-7.25 (m, 14H).

Example 5

Preparation of (3R,5R)-7-[2-(4-fluorophenyl)-4-(4-hydroxymethyl-phenylamino) carbonyl)-5-isopropyl-3-phenylpyrrol-1-yl]-3,5-dihydroxy heptanoic acid tert-butyl ester A mixture of [(4R,6R)-6-(2-{2-(4-fluorophenyl)-5-isopropyl-3-phenyl-4-[4-(tetrahydro-pyran-2-yloxy methyl)phenyl amino)carbonyl]-pyrrol-1-yl}ethyl)-2,2-dimethyl-[1,3]dioxan-4-yl]-acetic acid tert-butyl ester (0.8 g, 0.0015 mol, 1 equiv.) and a mixture of 1 N hydrochloric acid:methanol: tetrahydrofuran in the ratio 2:5:5 (24 mL) was placed in a single neck flask. The reaction mixture was stirred at room temperature. Reaction mixture was concentrated by evaporating solvent under reduced pressure. The crude compound was extracted with ethyl acetate and the ethyl acetate layer was washed with brine, dried over anhydrous sodium sulphate and concentrated. The crude mixture was purified on column (silica gel, 100-200 mesh, 60% ethyl acetate/hexane) to obtain the pure product. Yield: 446 mg (66.56%).

MS (+ion mode): m/z 645.32 (M+1); $^1$H NMR (CDCl$_3$, 300 Hz): δ 1.15-1.30 (m, 2H); 1.45 (s, 9H); 1.47-1.62 (m, 8H); 2.32 (d, J=6.0 Hz, 2H); 3.53-3.60 (m, 2H); 3.69-3.92 (m, 1H); 4.08-4.13 (m, 2H); 4.58 (s, 2H); 6.87 (s, 1H); 6.97-7.25 (m, 13H).

Example 6

Preparation of (3R,5R)-7-[2-(4-fluorophenyl)-4-(4-hydroxy methyl-phenyl amino) carbonyl)-5-isopropyl-3-phenyl-pyrrol-1-yl]-3,5-dihydroxy-heptanoic acid hemi calcium salt Step 1: (3R,5R)-7-[2-(4-fluorophenyl)-4-(4-hydroxy methyl phenyl amino) carbonyl)-5-isopropyl-3-phenylpyrrol-1-yl]-3,5-dihydroxyheptanoic acid tert-butyl ester in a mixture of methanol-tetrahydrofuran (1:1) was cooled to 0° C. and sodium hydroxide pellets were added. The reaction mixture was then stirred at an ambient temperature. At the end of ester hydrolysis, solvents were removed and the residue was dissolved in water, and the aqueous layer was washed with ether.

Step 2: To an aqueous solution of sodium salt of (3R,5R)-7-[2-(4-fluorophenyl)-4-(4-hydroxy methyl-phenyl amino) carbonyl)-5-isopropyl-3-phenyl-pyrrol-1-yl]-3,5-dihydroxy-heptanoic acid was added drop wise an aqueous solution (1M) of calcium acetate (0.55 equiv.). White precipitate was obtained, which was filtered off, washed with copious amount of water, and dried in vacuo. Yield=63.4%

MS (positive ion mode): m/z 589 (Acid+1); m.p.=189-204° C.; $^1$H NMR (DMSO-d$_6$): δ 1.22-1.62 (m, 11H), 1.98 (dd, J=15 & 8.1 Hz, 1H), 2.06-2.16 (m, 1H), 3.25-3.37 (m, 2H), 3.57 (brs, 2H), 3.80 (brs, 1H), 4.43 (s, 2H), 7.03-7.28 (m, 12H), 7.50 (d, J=6H, 2H), 9.80 (s, 1H)

We claim:
1. A method for the preparation of (3R,5R)-7-[2-(4-fluorophenyl)-5-isopropyl-3-phenyl-4-[(4-hydroxy methyl phenyl amino) carbonyl]-pyrrol-1-yl]-3,5-dihydroxy-heptanoic acid hemi calcium salt of Formula I,

Formula I

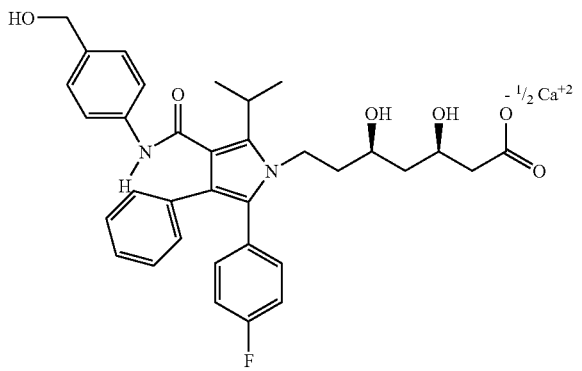

comprising:
(a) reacting an amine of Formula II with methyl isobutyryl acetate of Formula III Formula II

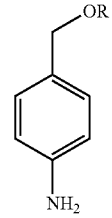

Formula III

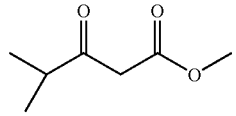

to form a compound of Formula of IV, wherein R is a hydroxy protecting group selected from the group consisting of acetyl, benzoyl, tetrahydropyranyl, methoxy methyl, methoxy ethoxymethyl, and benzyl;

Formula IV

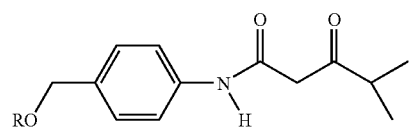

b) reacting the compound of Formula IV with benzaldehyde to form a compound of Formula V;

Formula V

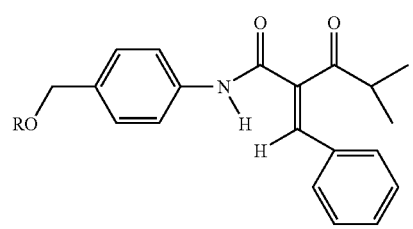

c) reacting the compound of Formula V with 4-fluorobenzaldehyde to form a compound of Formula VI;

Formula VI

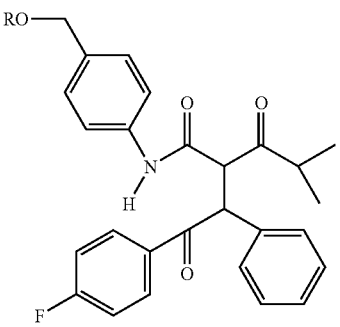

d) reacting the compound of Formula VI with a compound of Formula VII

Formula VII

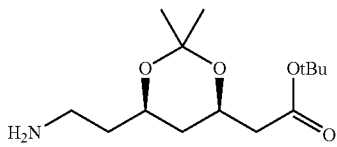

to form a compound of Formula VIII;

Formula VIII

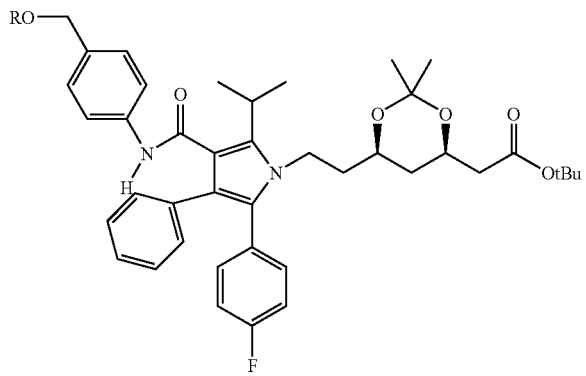

e) subjecting the compound of Formula VIII with a mineral acide simultaneously to induce acid-catalyzed cleavage of ketal and the hydroxy protecting groups to form a crude compound of Formula IX;

Formula IX

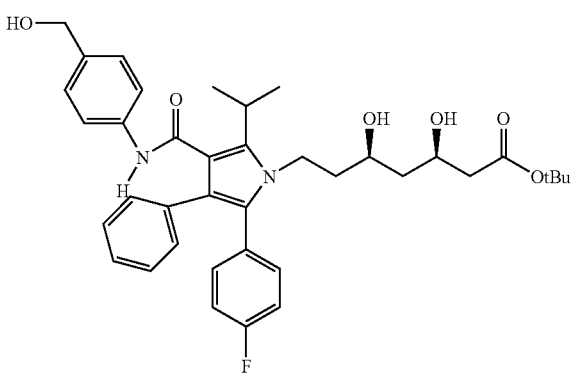

f) purifying the crude compound of Formula IX to form a purified compound of Formula IX;

g) subjecting the purified compound of Formula IX with a base to induce base-catalyzed hydrolysis to form a compound of Formula X; and Formula X

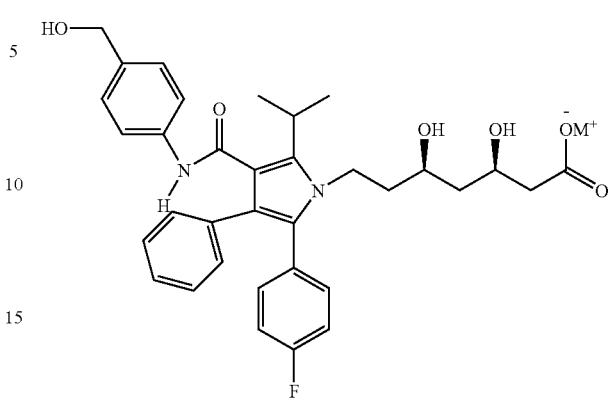

(wherein, M = Li, Na or K)

h) reacting the compound of Formula X with aqueous solution of calcium acetate to form a compound of Formula I.

2. The process of claim 1, wherein the reaction of the amine of Formula II is carried out
   i) in the presence of one or more organic bases; and
   ii) in one or more aromatic solvents.

3. The process of claim 1, wherein the reaction of the compound of Formula IV is carried out
   i) in the presence of one or more organic bases selected from the group consisting of piperidine, pyridine, and β-alanine; or in the presence off one or more organic acids selected from the group consisting of glacial acetic acid and benzoic acid; or in the presence of a mixture of organic bases or organic acids; and
   ii) in one or more solvents selected from the group consisting of hexane, heptane, dichloromethane, dichloroethane, chloroform, toluene, xylene, and mixtures thereof.

4. The process of claim 1, wherein the reaction of the compound of Formula V is carried out
   i) in the presence of one or more catalysts selected from the group consisting of sodium cyanide, 3-ethyl-5-(2-hydroxyethyl)-4-methyl thiazolium bromide, 3-benzyl-5-(2-hydroxyethyl)-4-methyl thiazolium chloride and mixtures thereof;
   ii) in the presence of one or more organic bases selected from the group consisting of triethylamine, pyridine and mixtures thereof; and
   iii) in a solvent-free condition or in one or more solvents selected from the group consisting of methanol, ethanol, propanol, isopropanol, water, dioxin, tetrahydrofuran, and mixtures thereof.

5. The process of claim 1, wherein the reaction of a compound of Formula VI is carried out
   i) in the presence of one or more organic acids selected from the group consisting of pivalic acid, p-toluene sulfonic acid, and mixtures thereof; and
   ii) in the presence of one or more solvents selected from the group consisting of xylene, toluene, hexane, and heptanes, tetrahydrofuran, dioxane, diethyl ether, and mixtures thereof.

6. The process of claim 1, wherein the cleavage of ketal and hydroxy protecting groups of the compound of Formula VIII is carried out i) in the presence of one or more mineral acids selected from the group consisting of hydrochloric acid, hydrobromic acid, hydroiodic acid, and mixtures thereof; and
ii) in the presence of one or more solvents selected from the group consisting of methanol, ethanol, propanol, water, tetrahydrofuran, diethyl ether, and mixtures thereof.

7. The process of claim 1, wherein the hydrolysis of a compound of Formula IX is carried out
   i) in the presence of one or more bases selected from the group consisting of lithium hydroxide, sodium hydroxide, potassium hydroxide and mixtures thereof; and
   ii) in the presence of one or more solvents selected from the group consisting of methanol, ethanol, propanol, isopropanol, water, tetrahydrofuran, diethyl ether, and mixtures thereof.

8. The process of claim 1, wherein the crude compound of Formula IX is purified by a column.

* * * * *